(12) United States Patent
Main et al.

(10) Patent No.: US 9,226,740 B2
(45) Date of Patent: Jan. 5, 2016

(54) SURGICAL INSTRUMENT

(75) Inventors: David Main, Leeds (GB); Michael White, Leeds (GB)

(73) Assignee: SURGICAL INNOVATIONS LIMITED, Leeds (GB)

( * ) Notice: Subject to any disclaimer, the term of this patent is extended or adjusted under 35 U.S.C. 154(b) by 20 days.

(21) Appl. No.: 12/996,885

(22) PCT Filed: Oct. 7, 2010

(86) PCT No.: PCT/GB2010/051680
§ 371 (c)(1),
(2), (4) Date: Jul. 15, 2011

(87) PCT Pub. No.: WO2011/042745
PCT Pub. Date: Apr. 14, 2011

(65) Prior Publication Data
US 2012/0232530 A1 Sep. 13, 2012

(30) Foreign Application Priority Data

Oct. 8, 2009 (GB) .................................. 0917559.7

(51) Int. Cl.
*A61B 1/32* (2006.01)
*A61B 17/02* (2006.01)
*A61B 17/29* (2006.01)

(52) U.S. Cl.
CPC ..... *A61B 17/0218* (2013.01); *A61B 2017/2908* (2013.01); *A61B 2017/2927* (2013.01)

(58) Field of Classification Search
USPC ....................................... 606/1; 600/185–209
See application file for complete search history.

(56) References Cited

U.S. PATENT DOCUMENTS

| 5,084,012 A | 1/1992 | Kelman |
| 5,308,342 A | 5/1994 | Sepetka et al. |
| 5,482,037 A | 1/1996 | Borghi |
| 5,662,606 A | 9/1997 | Cimino et al. |
| 5,879,352 A * | 3/1999 | Filoso et al. ................ 606/62 |
| 6,002,955 A | 12/1999 | Willems et al. |
| 6,067,990 A * | 5/2000 | Kieturakis .................... 606/1 |
| 6,248,062 B1 * | 6/2001 | Adler et al. ................ 600/204 |
| 6,277,089 B1 * | 8/2001 | Yoon ............................ 604/1 |
| 7,766,941 B2 * | 8/2010 | Paul ......................... 606/257 |

(Continued)

FOREIGN PATENT DOCUMENTS

| EP | 2 002 858 A2 | 12/2008 |
| GB | 456 165 A | 7/2009 |

(Continued)

OTHER PUBLICATIONS

International Search Report dated Jun. 12, 2010 for PCT/GB2010/051680.

(Continued)

*Primary Examiner* — Jan Christopher Merene
*Assistant Examiner* — Steven Cotroneo
(74) *Attorney, Agent, or Firm* — Shumaker, Loop & Kendrick, LLP

(57) ABSTRACT

A surgical instrument including an elongate portion arranged, in use, to be inserted through a restricted opening into a body, the elongate portion being movable from a first configuration to a second, different configuration in which two parts of the instrument that are spaced from each other in the first configuration at least partially cross each other in the second configuration.

9 Claims, 3 Drawing Sheets

(56) References Cited

U.S. PATENT DOCUMENTS

| | | |
|---|---|---|
| 2002/0111536 A1* | 8/2002 | Cuschieri et al. ............. 600/210 |
| 2006/0178562 A1 | 8/2006 | Saadat et al. |
| 2007/0112302 A1 | 5/2007 | Yu |
| 2008/0234691 A1* | 9/2008 | Schwab ........................ 606/100 |
| 2009/0079821 A1 | 3/2009 | Bousquet et al. |
| 2009/0281498 A1 | 11/2009 | Acosta et al. |

FOREIGN PATENT DOCUMENTS

| | | |
|---|---|---|
| WO | WO 93 13713 A1 | 7/1993 |
| WO | WO 93/13713 B1 | 7/1993 |
| WO | WO 98/48713 A1 | 11/1998 |
| WO | WO 01/23022 A1 | 4/2001 |
| WO | WO 2004/032757 A2 | 4/2004 |
| WO | WO 2004 032757 A2 | 4/2004 |

OTHER PUBLICATIONS

UK Search Report dated Jan. 26, 2010 for Patent Application No. GB 0917559.7.

Dec. 6, 2010 International Search Report issued in PCT/GB2010/051680.

* cited by examiner

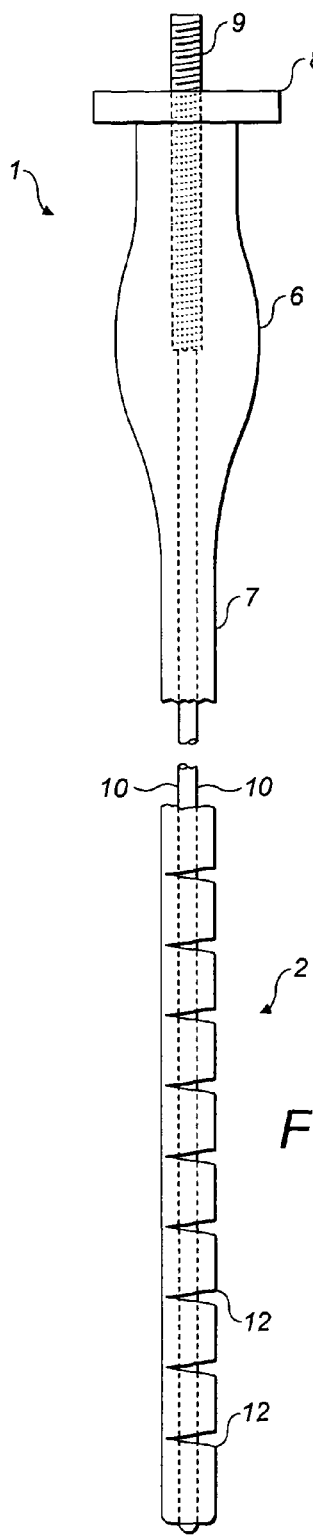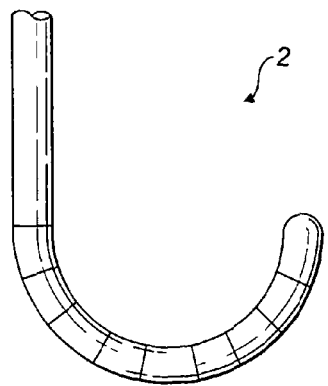
FIG. 2
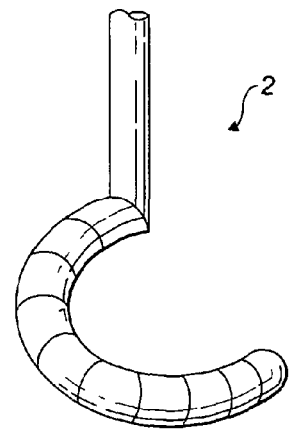
FIG. 3
FIG. 1
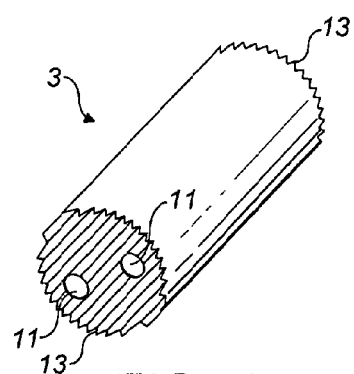
FIG. 4

SURGICAL INSTRUMENT

FIELD AND BACKGROUND OF THE INVENTION

The present invention relates to surgical instrument and a method of controlling a surgical instrument. The invention is particularly applicable to endoscopic surgical instruments.

EP 0 623 004 discloses a surgical instrument comprising a retractor.

SUMMARY OF THE INVENTION

Disclosed is a surgical instrument including an elongate portion arranged, in use, to be inserted through a restricted opening into a body, the elongate portion being movable from a first configuration to a second, different configuration in which two parts of the instrument that are spaced from each other in the first configuration at least partially cross each other in the second configuration.

BRIEF DESCRIPTION OF THE DRAWINGS

FIG. 1 is a side view of a surgical instrument comprising a surgical retractor 1 with an end 2 in a straight configuration;

FIG. 2 is a view of the end 2 of the retractor shown in FIG. 1 in a straight hook configuration;

FIG. 3 is a view of an end 2 of a retractor similar to that shown in FIG. 1 in an angled hook configuration and FIG. 4 is a schematic perspective view of one of the segments 3 at the end 2 of the retractor shown in FIG. 1.

DETAILED DESCRIPTION

Figure 5:
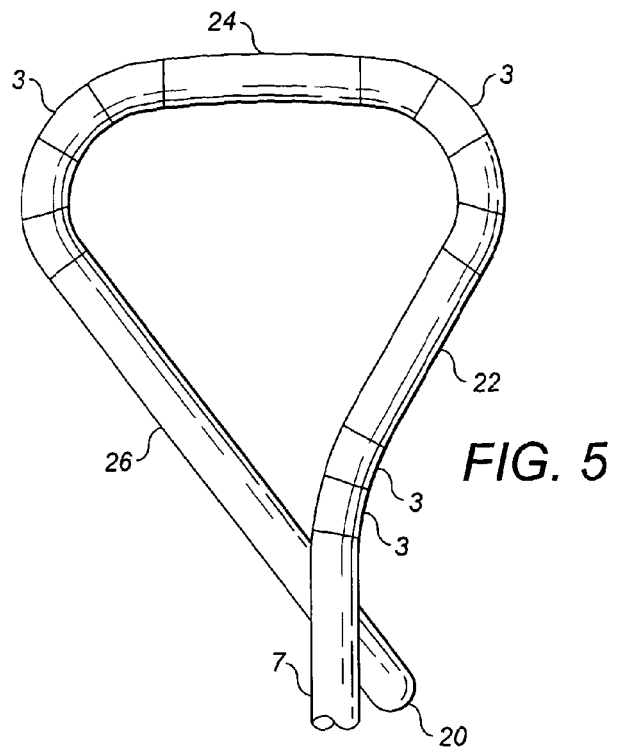
FIG. 5 is a front view of a first embodiment of a retractor.

FIG. 1 shows a retractor 1 having a handle 6 which is connected to the end 2 via a hollow rod 7. In use, with the end in the configuration shown in the drawing, the end 2 and part of the rod 7 are fed through a tube in the abdominal wall. The surgeon is then able to manipulate the retractor by the handle 6 and change the configuration of the end 2 into the straight hook shape shown in FIG. 2 by rotating a knurled actuating nut 8.

The nut 8 is threadably connected to a screw member 9 whereby, when the nut 8 is rotated in a clockwise direction, looking from the free end of the handle, the screw member 9 is caused to move translationally away from the end 2. A loop of wire 10 is connected at its free ends to the member 9, and both sides of the loop pass through openings 11 in each segment 3. Accordingly as the wire 10 moves further into the rod 7 the segments are caused to tighten against each other.

As the segments 3 bear against each other they are caused to move out of the axial extent of the rod as the end faces 12 of each segment are formed at a slight angle to the perpendicular to the axis of the rod. In FIG. 1 the upwardly facing surfaces of each segment are parallel with each other as are the downwardly facing surfaces. Accordingly adjacent faces come into abutment with each other as the wire is lightened, and they take up the configuration shown in FIG. 2 in which a straight, substantially rigid hook which subtends approximately 180° is formed. Accordingly in the position shown in FIG. 1, each face extends at an angle of approximately 10° to the axis of the tube.

In order for the segments to take up the shape shown in FIG. 3, in which a substantially rigid hook which subtends approximately 180° in a direction generally at right angles to the axis of the rod, the face of at least one of the segments is angled differently. For instance, when the end 2 is in the relaxed position and extends generally in line with the axis of the rod 7, the uppermost segment faces the rod with a face extending at 45° to the axis of the rod, and the rod may be correspondingly angled at its end. Thus when the wire is tightened, the segment adjacent to the rod is caused to turn through 90°. The remaining upper and lower faces of the other segments may be parallel to each other in the configuration shown in FIG. 1 as previously described.

The hooks shown in FIGS. 2 and 3 can be used to displace or hold the organs in the required position.

To release the segments from the configuration shown in FIG. 2 or 3 the nut 8 is rotated in the opposite direction to release the tension in the wire. The wire is sufficiently strong, and the distance between the segments sufficiently small for the flexure of the wire to hold the segments generally straight for ease of insertion or removal when the hook configuration is not required. As the wire is threaded through two openings in each segment the strength of the wire and the close proximity of the segments prevents any significant relative turning of the segments around the longitudinal extent of the end 2.

The face of each segment which is caused to abut against another part of the retractor when in the hook configuration is formed with styrations 13 which are parallel to each other and parallel to adjacent styrations such that co-operating faces do not tend to slip in a rotational or translational sense.

With such retractors the remote end includes an exposed end 20. When pushing tissue aside this end can cause trauma to the body, particularly the liver. In addition there is inevitably some flexure in the segments. Such flexure causes the end section to have a reduced effect on pushing the liver.

Furthermore, whilst it is relatively easy to achieve the configuration shown it can be difficult to effect more complicated configurations.

It is an object of the present invention to attempt to overcome at least one of the above or other disadvantages.

According to one aspect of the present invention a surgical instrument includes an elongate portion arranged, in use, to be inserted through a restricted opening into a body, the elongate portion being movable from a first configuration to a second, different configuration in which second configuration two parts of the instrument that are spaced from each other in the first configuration at least partially cross each other in second configuration.

According to a further aspect of the present invention a method of controlling a surgical instrument comprises causing an elongate portion to move from a first configuration in which two parts are spaced from each other to a second configuration in which those parts at least partially cross each other.

The present invention also includes a method of performing surgery when using the instrument of the present invention or when controlling the instrument of the present invention.

The first configuration may be a straight configuration.

Each of the embodiments of the retractors shown may be operated as described in relation to FIGS. 1 to 4. Accordingly only the differences will be described. In addition, each retractor is able to have a straight configuration to enable the retractor to be inserted or removed and only the second configurations are shown in which each adjacent segment abuts each other to inhibit further bending.

In FIG. 5 there are four segments 3 adjacent to the hollow rod 7 and four at each of the further corners. Long segments 22 and 24 extend between the short segments and a longer segment 26 has its tip 20 extending back under the rod 7. Ideally the tip 20 should be concealed in the view shown by the hollow rod.

This arrangement has advantages over the segmental arrangements shown in FIGS. 2 and 3 in that no twisting of the retractor about the shaft 7 occurs if the retractor is urged in a direction out of the plane shown or into the plane shown. In addition at least part of the tip 20 is concealed by the rod 7 or can trail the rod 7 thus effecting less trauma.

Figure 6:
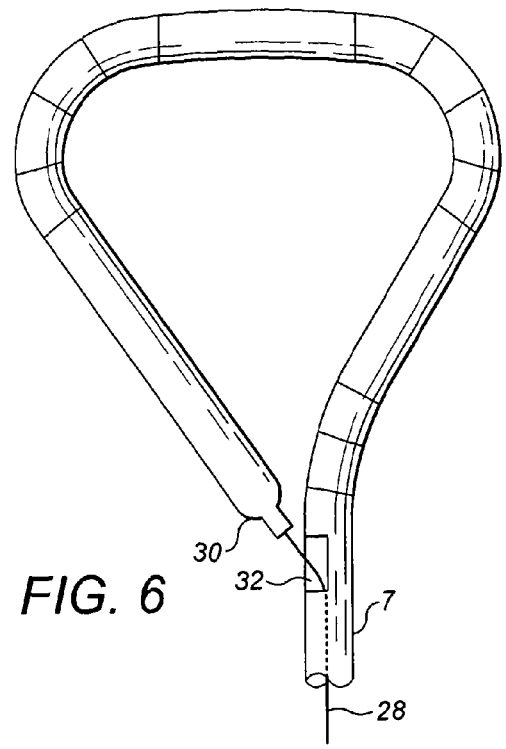
FIG. 6 is a front view of a second embodiment of a retractor.

FIG. 6 has the same general shape of that of FIG. 5. However the shaft 7 includes a further control cable 28 that is connected to the tip 30 of the elongate portion. The cable exits the shaft 7 just short of the first series of segments.

In use, either before the segments are tensioned by the wires 10 to take up the configuration shown, or after, or during at least part of that tensioning or any combination thereof the control cable 28 is tensioned to draw the tip 30 towards the shaft 7. A recess 32 may be provided in the shaft 7 in which the tip 30 may be drawn into and held by the cable.

This configuration allows greater force to be applied with less trauma being provided than that of FIG. 5. In addition the retractor can be urged in either direction to equal advantage as the configuration is symmetrical from the front and back.

Figure 7:
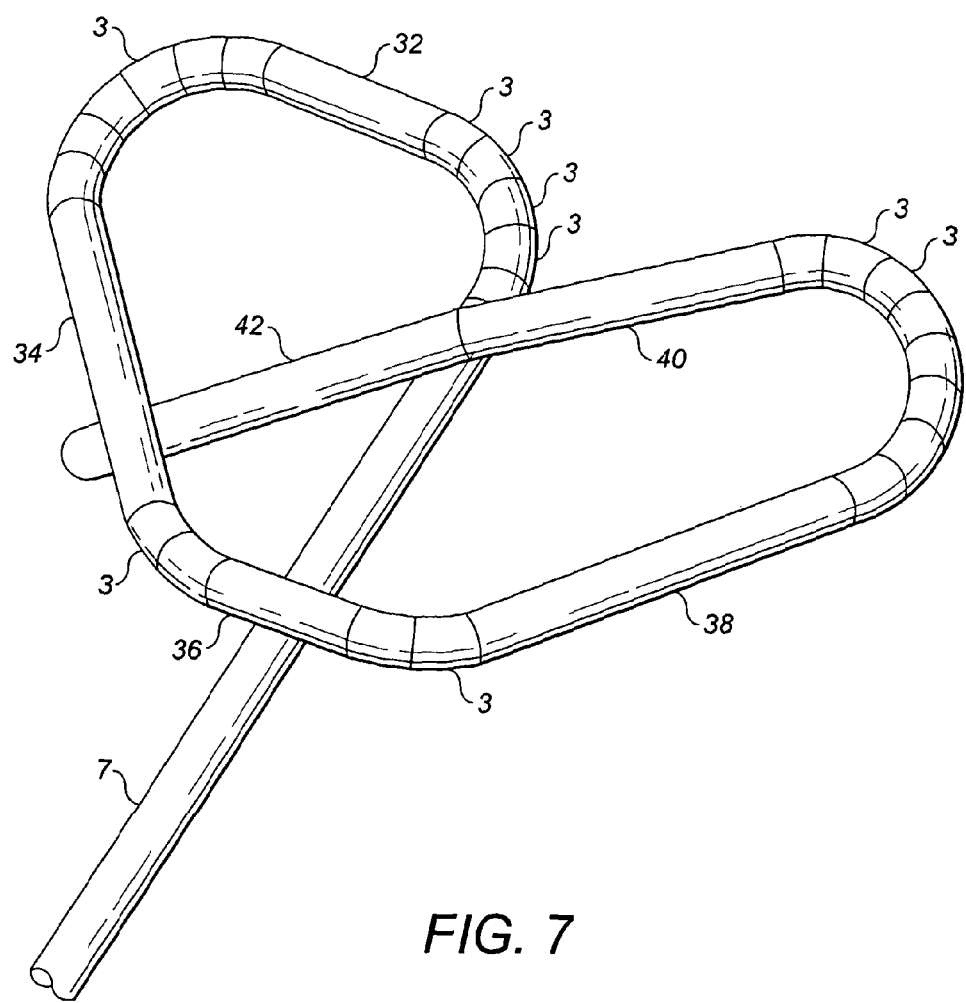
FIG. 7 is a perspective view of a third embodiment of a retractor.

Whilst the angles that the short segment of FIGS. 5 and 6 allow the retractor to turn are approximately 45°, 135° and 135° respectively the embodiment of FIG. 7 is more complicated.

In FIG. 7, starting from the rod 7, four short segments 3 allow the next long segment 32 to extend at 90° to the extent of the rod. Then six short segments 3 cause an even longer segment 34 to extend back towards the rod 7 at an angle of 45° to the rod. Then two short segments cause the "shortest" long segment 36 to cross over the rod 7, possibly in contact therewith, before two further short segments cause a further turn of 45° for the next long segment 38. Then eight short segments 3 cause a further turn of 180°. This brings two long segments 40 and 42 back over the rod 7 with the end of the segment 42 being tucked under the long segment 34.

The long segments 40 and 42 are connected by angled faces that allow the segment 40 to be inclined upwardly as it extends towards the rod with the segment 42 being inclined downwardly as it extends away from the rod 7. The movement of the segments 40 and 42 can be coordinated to take place as the end of the instrument moves back over the shaft towards the segment 34. Alternatively the segments 40 and 42 may be fixed together to form an angled suit such that they can not move relative to each other. The segments 40 and 42 may be urged against the long segment 32 and the short segments 3 adjacent to the rod 7 as the segments 40 and 42 are being moved into place such that relative flexure of those parts occurs. When the joint between the segments 40 and 42 pass the segments 3 adjacent to the rod they spring back to allow the segment 42 to pass beneath the segment 34 and to maintain the shape shown under flexure with those parts crossing the rod being urged against the rod. Furthermore, that binding force may also cause the segment 36 to be biased. The biasing forces may be assisted by the angled slope of the segment 42 sliding along the segment 34 and pushing further against the segment 34 as the segment 42 slides further beneath the segment 34.

The configuration of FIG. 7 affords stability and strength in either direction. Furthermore trauma is reduced because of the considerable cross sectional area provided by the retractor or both sides of the shaft 7.

Although not shown in the drawing of FIG. 7, the end segment 42 may be connected to the shaft 7 by a control cable. The control cable may be tensioned to assist in the retractor leaving the straight configuration. As the wires tension the segments and as the retractor takes up the shape shown the cable may be tensioned or relaxed to assist in the shape being taken up.

As the retractor crosses the rigid rod in FIGS. 5 and 7 (and as the retractor is fixed in FIG. 6) when the rod is urged towards a liver with the cross parts being located between the rod and liver a rigid retractor is provided with a broad area of even force being applied.

Whilst the above described instruments are retractors it will be appreciated that the instrument could be other than a retractor or may, for instance, have a tool operating from the end such as a cutter or a gripper of a suture.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A surgical instrument, comprising a retractor, including an elongate insertion portion adapted for being inserted through a restricted opening into a body, the elongate insertion portion having:
   (a) a plurality of adjacent joint segments that are collectively moveable relative to each other to define a predetermined shape of the elongate insertion portion;
   (b) a plurality of individual rigid joint segments interspersed and positioned between selected ones of the plurality of adjacent joint segments along a length of the surgical instrument and a pair of immediately adjacent rigid joint segments positioned at an end portion of the surgical instrument, wherein;
   (c) the plurality of individual rigid joint segments and pair of immediately adjacent rigid joint segments positioned at the end portion of the surgical instrument each have a greater length along the length of the surgical instrument than each adjacent joint segment;
   (d) the plurality of individual rigid joint segments and the pair of immediately adjacent rigid joint segments positioned at the end portion of the surgical instrument are movable between a first configuration; and
   (e) a second configuration wherein the plurality of adjacent joint segments define curves, and the plurality of individual rigid joint segments and pair of immediately adjacent rigid joint segments positioned at the end portion of the surgical instrument are configured to selectively cross one another to form a pretzel shape configured to stably support a body organ in the second configuration.

2. An instrument as claimed in claim 1 in which at least one rigid joint segment and adjacent joint segment that is collectively moveable are spaced from the end region.

3. An instrument as claimed in claim 1 in which, in the first configuration, the instrument extends in a common first direction and in which, in the second configuration part of the instrument extends in a second direction which is opposed to the first direction.

4. An instrument as claimed in claim 3 in which, in the second configuration, at least two of the plurality of adjacent joint segments, extend in a first direction that is at an angle to a second direction.

5. An instrument as claimed in claim 1, including a first control means arranged to cause movement from the first configuration to the second configuration.

6. An instrument as claimed in claim 1 in which, in the second configuration, two of the rigid joint segments are biased towards each other where they cross.

7. An instrument as claimed in claim 1, including a flexible member extending outside of the instrument from an end region to a location spaced from the end region.

8. An instrument as claimed in claim 7 in which the flexible member is arranged to assist in effecting movement from the first configuration to the second configuration.

9. An instrument as claimed in claim 8 in which the flexible member is arranged to be initially tensioned, as movement from the first configuration commences and subsequently to be slackened.

\* \* \* \* \*